United States Patent [19]
Alt et al.

[11] Patent Number: 5,342,404
[45] Date of Patent: Aug. 30, 1994

[54] IMPLANTABLE MEDICAL INTERVENTIONAL DEVICE

[75] Inventors: Eckhard Alt, Ottobrunn; Marcus Matula, Munich; Edgar Mestre, Munich, all of Fed. Rep. of Germany

[73] Assignee: Intermedics, Inc., Angleton, Tex.

[21] Appl. No.: 863,092

[22] Filed: Apr. 3, 1992

[51] Int. Cl.$^5$ ............................................. A61N 1/39
[52] U.S. Cl. ........................................ 607/6; 607/14; 607/19; 128/782
[58] Field of Search ................. 128/782; 607/6, 14, 607/18, 19

[56] References Cited

U.S. PATENT DOCUMENTS

| | | | |
|---|---|---|---|
| 4,771,780 | 9/1988 | Sholder | 128/782 |
| 4,836,218 | 6/1989 | Gay et al. | 128/782 |
| 5,014,698 | 5/1991 | Cohen | 607/6 |
| 5,031,614 | 7/1991 | Alt | 607/19 |
| 5,040,535 | 8/1991 | Mann et al. | 607/19 |
| 5,097,831 | 3/1992 | Lekhulm | 607/18 |
| 5,233,984 | 8/1993 | Thompson | 128/782 |

FOREIGN PATENT DOCUMENTS 0360412  3/1990  European Pat. Off. .............. 607/18

*Primary Examiner*—William E. Kamm
*Attorney, Agent, or Firm*—O'Connor Cavanagh

[57] ABSTRACT

An implantable medical interventional device responds to detection of cardiac activity of the patient indicative of ventricular tachycardia (VT) or fibrillation (VF) by successively applying to the patient's heart selected ones of different electrical waveforms for treatment to break the VT or VF, respectively, until the monitored cardiac activity indicates that the treatment has been successful. An accelerometer adapted to sense position and movement of the patient along three mutually orthogonal axes acts as an activity status sensor to detect physical activity and inactivity of the patient to complement the detection of the patient's cardiac activity for confirming that a detected VT is a pathologic tachycardia rather than a physiologic tachycardia, and in response to such confirmation the device selects an appropriate electrical waveform for the treatment. The device is capable of recognizing from detected physical activity the occurrence of a sudden vigorous movement associated with a syncope by calculating variances relative to the mean of the detected physical activity, and of responding to such recognition by selecting a defibrillating waveform for immediate application to the patient's heart. A scoring system based on assigned weightings of subparameters of detected cardiac activity and detected physical activity or inactivity is used to determine the likelihood that a physiologic tachycardia, a pathologic tachycardia, or fibrillation is being detected.

29 Claims, 4 Drawing Sheets

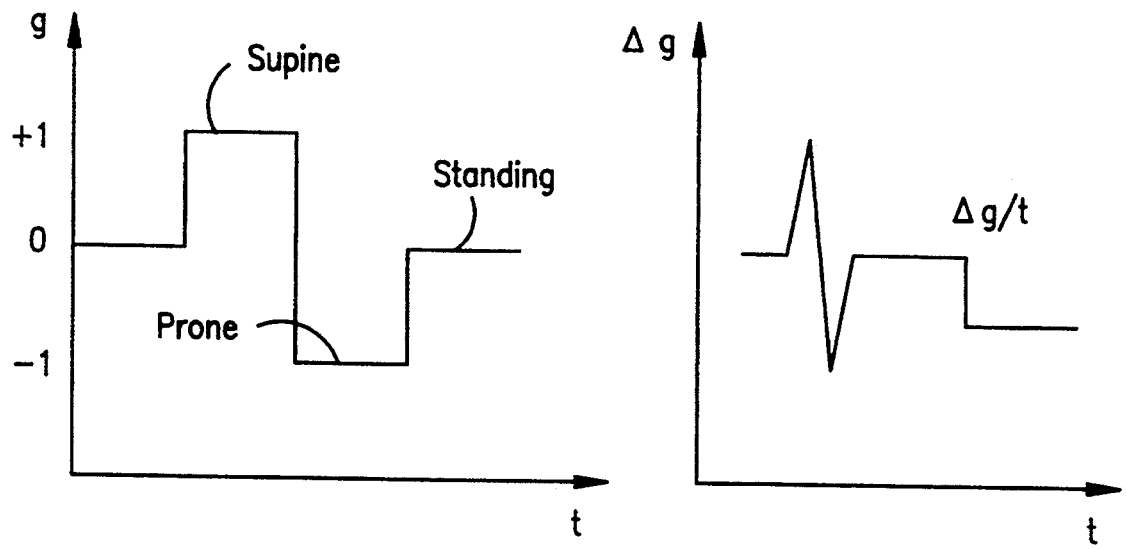
FIG. 1
FIG. 2
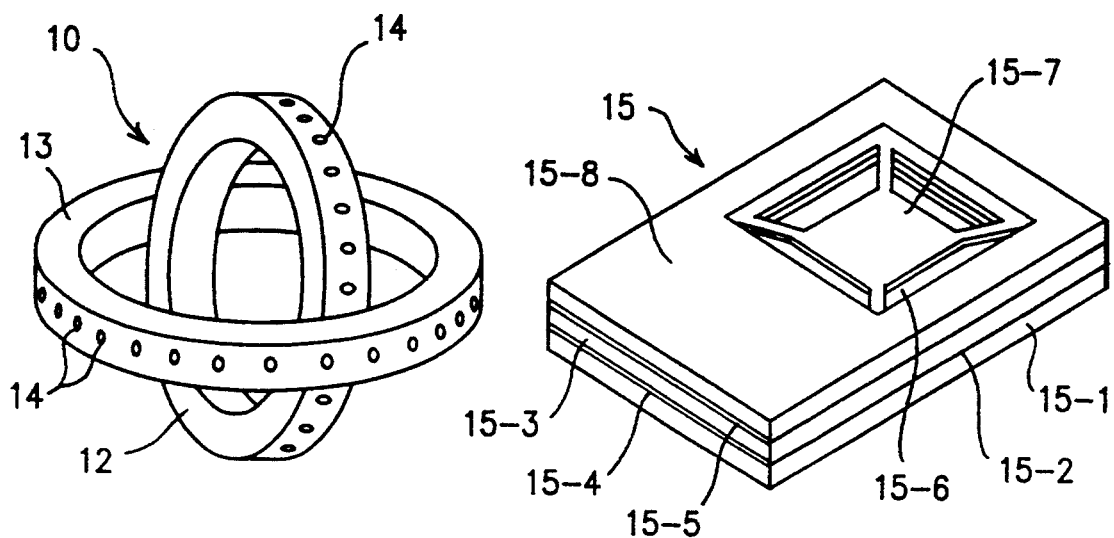
FIG. 3A
FIG. 3B

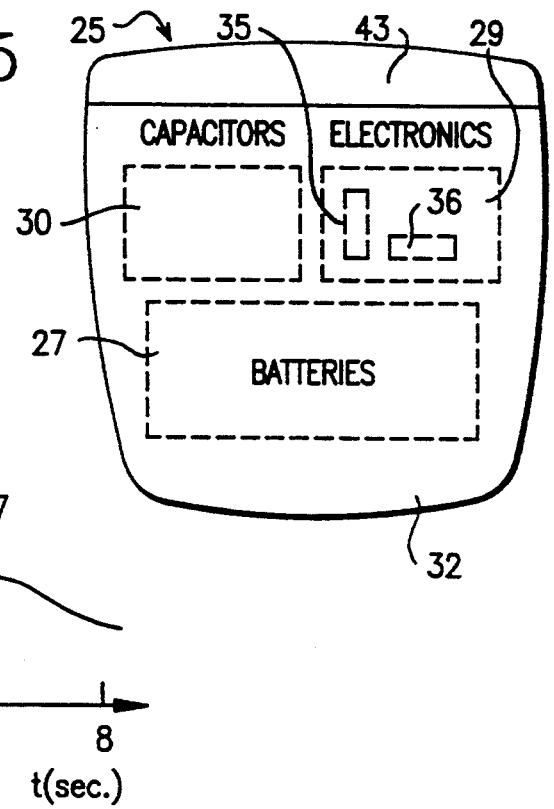
FIG. 5
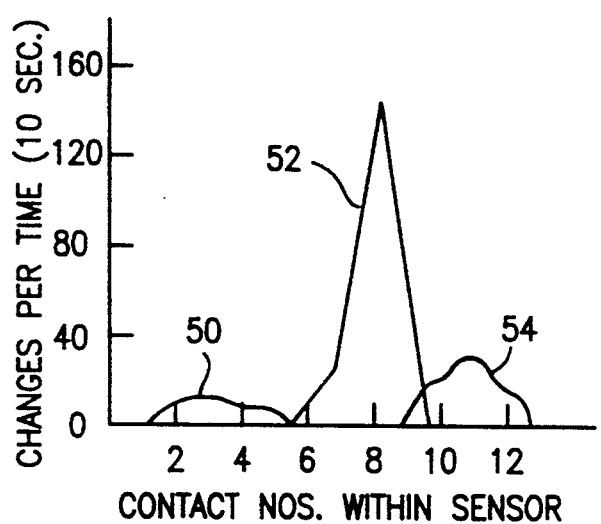
FIG. 4
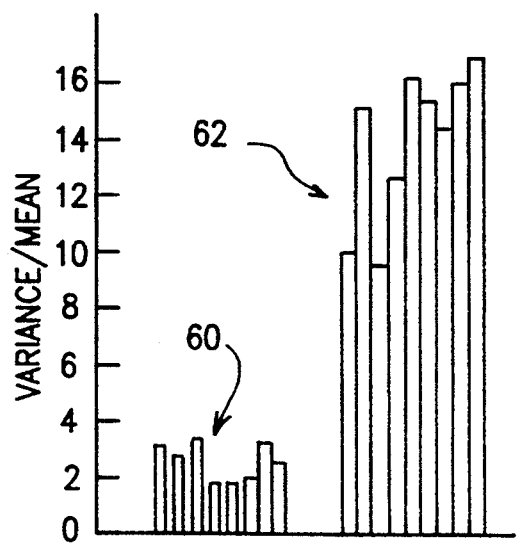
FIG. 6
FIG. 7

IMPLANTABLE MEDICAL INTERVENTIONAL DEVICE

BACKGROUND OF THE INVENTION

The present invention relates generally to implantable medical devices, and more particularly to an implantable interventional device which is adapted to deliver electric impulse or shock therapies to the patient's heart upon detection of a ventricular tachycardia (VT) or ventricular fibrillation (VF), and to improvements in apparatus and methods for detecting and distinguishing pathologic tachycardias from physiologic tachycardias and for establishing the timing of the delivery of the appropriate therapy upon detection of pathologic VT or VF.

Sinus heart rates in normal healthy adults typically range upward to 160 beats per minute (bpm) during physical activity or exercise, emotional stress or excitement, or under the influence of various drugs including alcohol, caffeine or nicotine. Even higher rates, to 200 bpm may be experienced during strenuous exercise. Rates exceeding 100 bpm in these and similar circumstances are physiologic tachycardias. The heart rate of an individual with a normal healthy cardiovascular system will gradually, perhaps even quickly, decrease toward his or her customary resting rate when the factors leading to the increased rate have ceased.

In contrast, pathologic tachycardias are abnormal, arising from cardiovascular disease or disorders, and require medical treatment and appropriate therapy. A pathologic tachycardia occurring in the atrial chamber is usually hemodynamically tolerated because the excitable A-V junction tissue (between the atrium and ventricle) has a longer refractory period and slower conductivity than myocardial tissue. Hence, the rapid atrial contractions during atrial tachycardia typically will not induce correspondingly rapid ventricular contractions, but rather a ventricular rate of one-half or even one-third in the A-V conduction. Cardiac output remains relatively strong with a ventricular rhythm within or close to sinus rate.

However, pathologic tachycardia in the ventricles, the main pumping chambers of the heart, is not well tolerated because of the diminished cardiac output attributable to only partial filling of the chambers with oxygenated blood between the rapid contractions. Moreover, ventricular tachycardia (VT) tends to accelerate spontaneously to ventricular fibrillation (VF), in which the myocardial contractions become random and uncoordinated. Unlike atrial fibrillation, which is generally not life-threatening because of the relatively small percentage of cardiac output contributed by the atria, VF is characterized by the loss of synchronous contractions of the tissue in the main pumping chambers. The resulting drop in cardiac output will lead to death in minutes unless adequate cardiac output is restored within that interval.

Atrial tachycardia is relatively common, but patients who are symptomatic or at high risk may be treated with drugs, antitachycardia pacemakers, or in some extreme cases, including patients who suffer from atrial fibrillation, by performing a surgical A-V block and a ventricular pacemaker implant. The antitachycardia pacemakers, also used in patients who suffer VT, generally operate on the principle of overstimulating the heart (at a programmed rapid rate or variable rates) to suppress the ectopic activity that leads to premature atrial or ventricular contractions. Only pulses of relatively low energy content may be required to provide the desired stimulation. Interestingly, previous techniques used for terminating atrial flutter include high rate pacing of the atrium exceeding the flutter rate in an attempt to trigger atrial fibrillation, and spontaneous rapid reversion to normal sinus rhythm. In a technique sometimes referred to as cardioversion, tachycardia is broken by delivering higher energy electrical shocks to the heart. Unfortunately, antitachycardia and cardioversion therapies used for terminating VT can cause acceleration into VF.

Defibrillators are employed to apply one or more high energy electrical shocks to the heart to overwhelm the uncoordinated contractions of the various sections of the myocardial tissue and reestablish organized spreading of action potentials from cell to cell, and thereby restore synchronized contractions of the ventricles. Automatic implantable defibrillators were described in the literature at least as early as 1970, in separate articles of M. Mirowski et al. and J. Schuder et al. Steady innovations proposed since that time have included automatic implantable defibrillators which perform multiple functions of antitachycardia, cardioversion and defibrillation, and where appropriate, demand bradycardia pacing. In general, the desire is to use one or more pulse sequence or low level shock therapies for breaking VT before it spontaneously accelerates into VF, and, if that fails or if VF occurs without preliminary pathologic tachycardia, to resort to a high energy defibrillating shock.

The shocks, both lower energy for antitachycardia and high energy for defibrillation, are typically delivered from one or more output storage capacitors in the implanted device which are of sufficient size to store the electrical charge necessary for these functions. Energy requirements generally range from as little as 0.05 joule to up to 10 joules for cardioversion, and from 5 joules to about 40 joules for defibrillation, depending on the patient, the nature of the electrical waveform applied, and the efficiency of the energy transfer through the electrodes and into the heart tissue. It is imperative, particularly where VF is occurring, that the required energy be available at the time the shock is to be delivered. Multiphasic shocks have been found effective, and in any event, it is customary to provide a preset delay between successive shocks, and to inhibit further shocks when return to normal rhythm is detected.

As used in this specification, the terminology "shock" or "shocks" may include any pulse-type waveform, whether single phase or multiphase, which is delivered as antitachycardia, cardioverting or defibrillating therapy to a patient's heart in an effort to break, interrupt or terminate pathologic tachycardia or fibrillation and return the pumping action of the heart to a rate in the normal range; and "interventional device" includes any antitachycardia pacemaker, cardioverter, defibrillator or other device or combination thereof which is adapted to be implanted or otherwise worn by a human or animal subject for the purpose of intervening to deliver shocks to the heart in response to detection of an abnormally rapid heart rate. The waveform is not limited to any particular energy content or range of energy content, and indeed, the therapy may include burst stimulation or other conventional techniques for applying stimulation pulses (such as for rapid pacing) to break a VT.

The operation of implantable antitachycardia pacemakers, cardioverters, defibrillators and similar medical devices raises problems concerning the timing of delivery of the therapy, such as the timing of charging and firing of shock-producing output capacitors. In the first instance, it is necessary to distinguish between physiologic tachycardia and pathologic tachycardia to assure that the capacitors are not needlessly charged either from states of full or partial depletion (discharge), and in the second instance, to guard against premature firing and discharge into the heart. U.S. Pat. No. 4,114,628 discloses an implantable device which automatically applies a defibrillating impulse to the patient's heart only when a predetermined time interval passes without cardiac activity. More elaborate detection schemes have been suggested. For example, in U.S. Pat. No. 3,805,795, the defibrillating shock is delivered upon detection of an absence of both electrical and mechanical physiological functions for a predetermined time interval.

In general, the prior art devices detect ECG changes and/or absence of a mechanical function such as rhythmic contractions, pulsatile arterial pressure, or respiration, and, in response, deliver the appropriate fixed or programmable therapy. Various types of additional sensors have been used for the latter functions, including pressure sensors in the heart, impedance measurements in the heart, flow probes in the aorta, flow probes in the pulmonary tract, and other extra-pacemaker or extra-defibrillator sensors, These sensors have not proved to be fully accurate or reliable.

It is a principal object of the present invention to provide improved techniques for treating ventricular tachycardia and/or fibrillation, including improved techniques for detecting tachycardia and distinguishing the normal physiologic type from the abnormal pathologic type.

A related object is the use, for such techniques, of a sensor which may be housed in the implanted interventional device itself or separately implanted, to detect position, change of position, and physical activity (or lack thereof) of the patient, and which applies an algorithm to reinforce or confirm (or contest or rebut) the ECG criteria, to improve the reliability of the decision regarding the propriety and timing of the intervention therapy available from the device.

SUMMARY OF THE INVENTION

According to a principal aspect of the present invention, the decisions on timing of the application of a selected antitachycardia and/or defibrillation therapy such as timing of charging and firing of output capacitors of an implanted interventional device are based, in part, on sensing resting position, change in position, or activity (physical movement or exercise) of the patient and generating an electrical signal representative thereof (referred to throughout this specification as the "activity status signal" whether the signal denotes movement ranging from slow to vigorous, or rest in the sense of inactivity or positional changes ranging from slight to pronounced) which, in conjunction with a complementary electrical signal from another source, such as from detection of the patient's cardiac activity (e.g., electrocardiogram or ECG, hereinafter referred to as the "ECG waveform" or "ECG signal"), is indicative of VT or VF. Importantly, the two sensed criteria are selected to reinforce (or possibly rebut) one another, and further proof of VT or VF (or lack of same) is obtained by calculating the mean and the standard deviation of the activity status signal. This provides the beneficial result of considerably better discrimination between a physiologic tachycardia, attributable for example to strenuous activity or exercise, and a pathologic tachycardia arising from a cardiac or cardiovascular disorder.

Using these criteria, the interventional device is adapted to make a decision to deliver an appropriate electrical shock or shocks (e.g., a pulse sequence of appropriate energy content) to the patient's heart (the ventricular myocardium) through implanted epicardial and/or endocardial electrodes (which may include so-called "patch" electrodes) connected to the implanted device, or not to do so, according to whether the patient is undergoing a non-physiologic (pathologic) tachycardia or a physiologic tachycardia, respectively. The rule by which this decision is made (the "decision rule") is implemented by appropriate programming of the interventional device to recognize the significance of confirming or rebutting evidence from the two signals. Either one of the sensor which produces the activity status signal (hereinafter referred to as the "activity status sensor") or the ECG sensor may be regarded as the primary, secondary or complementary sensor of rapid heart rate criteria which together evoke the decision rule on whether to apply interventional therapy.

Preferably, the activity status sensor is located within the case that houses the implanted interventional device but alternatively, it may be implanted separately in its own housing. In either event such a sensor is to be mechanically isolated from the case to avoid false readings attributable to pressure on the case. The ECG sensor, which receives signals from the heart via the sensing electrode and associated lead, would generally be disposed within the interventional device case. The activity status sensor output is used to complement the output of the ECG sensor. For example, the ECG signal may indicate a VT of 150 bpm which is in the range of both pathologic and physiologic tachycardia, but the activity status sensor detects physical activity, thereby forestalling delivery of antitachycardia treatment. On the other hand, the ECG may demonstrate VT or VF at a time when the activity status sensor is indicating that the patient is not moving, or has just undergone sudden brief vigorous movement characteristic of a syncope (loss of consciousness), leading to the decision to trigger prompt therapy. The decision, therefore, is a reasoned one and is made automatically, and in the case of origin of a tachycardia, discriminates between physiologic and non-physiologic.

If, despite the application of therapy from the implanted device, the tachycardia rate increases, the patient may then lose consciousness and, if he is standing, collapse. The activity status sensor would detect this and produce a commensurate output which, upon virtually instantaneous analysis, would lead to a conclusion that immediate, more stringent therapy is required. In this particular example, a defibrillating shock would be triggered.

The decision rule for applying therapy and the nature of the therapy may be implemented, in part, by calculating the quotient of the standard variation and the mean of the continuously monitored activity status sensor signal. This sensor is preferably an accelerometer which may be of the mercury ball type, or other activity indicator utilizing mechano-electrical converting element(s) capable of detecting position and movements of the patient, such as a silicon based piezoelectric, piezocapacitive, or piezoresistive sensor responsive to gravity and acceleration. In the preferred embodiment, the activity status sensor generates signals as a result of patient orientation or movements along any of three mutually orthogonal axes by means of an orthogonally oriented pair of mercury ball sensors. Such sensors undergo change in internal electrical connections as the orientation or acceleration of the sensor changes. When implanted, the sensor displays a fixed electrical connection or set of connections for a resting (or at least inactive) patient, or a varying number and location of electrical connections which are intermittently disrupted by movements of the patient.

Each mercury ball sensor has an array of electrical contacts across which the mercury ball may roll, so that the ball makes and breaks adjacent electrical contacts as it rolls in response to patient movements. According to an aspect of the invention, the number of variances (standard deviation) of the making and breaking of electrical connections from the mean number of electrical connections made and broken within a predetermined time interval is used to ascertain the nature of the activity or lack thereof, and whether or not it confirms the detection of a dramatic hemodynamic event warranting delivery of a more drastic therapy. Thus, the activity status sensor has the capability to distinguish patient activity from inactivity, as well as postural changes, to an extent that the conditions under which a defibrillating shock should be delivered to the patient's heart are readily discerned.

Alternatively, however, the implantable antitachycardia device may itself consist at least partially of hybrid electronic circuitry, so that the accelerometer is advantageously a mechanoelectrical converting element integrated into the hybrid electronic circuitry for control of the therapeutic functions of device, and, as noted above, the mechanoelectrical converting element is silicon based.

Accordingly, another object of the invention is to determine from the standard deviation relative to the mean of a signal indicative of activity status of the patient over time, the precise instant at which a defibrillating shock should be applied to the heart.

The quotient of the standard deviation and the mean or physiologic statistical norm of the activity status signal is calculated to determine whether the signal is consistent with normal physiological activity or indicative of a sudden and vigorous movement associated with a syncope. A random occurrence such as a syncope exhibits a high standard deviation, whereas the more constant signals associated with true physiological activity and exercise such as walking display a considerably lower variation from the mean or physiologic statistical norm. Therefore, this calculation can provide a clear confirmation of what appears to be a fast VT or VF from the reading of cardiac activity such as an ECG. The mean and the standard deviation of the activity status signal are determined, and the latter is divided by the former, by the microprocessor of the implanted medical interventional device.

For greater reliability, the activity status sensor signal is processed to compare the standard deviation and the mean over time, which is better suited to low level activity signals. A running average of the comparison may be calculated in blocks of time, such as one second each over a substantially longer time interval such as 32 seconds, for example, and each block processed on a first in - first out basis, to eliminate minor perturbations such as noise. This technique is useful not only to distinguish noise or spasmodic reactions from true exercise, but additionally to differentiate between different types of physical exercise. Furthermore, calculation of the standard deviation relative to the mean of the activity status signals to differentiate distinct types of exercise can be applied to signals derived from changes in intrinsic physiological parameters (such as blood temperature, respiration, etc.) as indicative of exercise, as well.

Therefore, it is another object of the invention to provide techniques for detecting collapse or evidencing other dramatic hemodynamic changes of the patient by calculating the standard deviation relative to the mean of signals derived from an activity status sensor or from any other sensor representing intrinsic physiological parameters, for confirming ECG evidence of pathologic tachycardia or fibrillation, to trigger the application of appropriate electrical waveform therapy to the patient's heart.

In a method of controlling the therapeutic function of an implantable antitachycardia device according to the invention, an electrical signal is generated representing sensed variations of an intrinsic physiologic parameter indicative of the substantially instantaneous hemodynamic condition of the implant patient, the mean and the standard deviation of the generated signal are calculated over a predetermined time interval, the quotient of the standard deviation and the mean over that time interval is calculated to determine therefrom a sudden hemodynamic change in the patient, and the function of the antitachycardia device is controlled in response to a determined sudden hemodynamic change. Here again, the intrinsic physiologic parameter to be sensed may be blood pressure, blood oxygen content, minute ventilation, central venous temperature, pulse rate or blood flow of the patient, or other known parameters. The therapeutic function of the device may include defibrillation, and that function may be triggered upon determination of a sudden hemodynamic change indicative of a drop in cardiac output exceeding a predetermined threshold level.

To further enhance the probability that the cardiac activity being detected warrants delivery of an appropriate therapy, and thereby avoid unnecessary and undesirable application of shocks, a scoring system may be used in which various parameters of the ECG and activity status signals are scored by weighting parameters of the signals according to the significance of their representations, and then tallied and compared against levels or degrees of probability that a particular cardiac event of interest is indicated.

According to the invention, a method of determining the timing for applying selected antitachycardia and defibrillating electrical therapies to a patient's heart from an implanted interventional device such as an automatic implanted defibrillator includes detecting the patient's cardiac activity to recognize a VT, while simultaneously detecting the current status of physical activity or inactivity of the patient, determining whether the recognized VT is physiologic or pathologic by comparing the detected cardiac activity with the detected status of physical activity or inactivity, and delivering an antitachycardia electrical therapy when the comparison indicates a pathologic tachycardia. A further aspect of the method is weighting the detected cardiac activity and the detected status of physical activity or inactivity as separate indicia of the degree of probability that a pathologic tachycardia is occurring, and tailoring the delivery of therapy according to the degree of probability indicated by the weighting. Defibrillating electrical therapy is delivered if the antitachycardia electrical therapy proves ineffective to terminate the tachycardia coupled with an indication of acceleration into VF.

According to the invention, a method of determining when to apply any of a plurality of available antitachycardia therapies, including possible defibrillation, to the patient from the implanted antitachycardia device includes detecting at least two different physiologic parameters of the patient, one of which represents electrical cardiac activity of the patient, processing the detected different physiologic parameters to obtain a variety of subparameters, scoring each of the processed subparameters by assigning to it a relative value according to its importance in signifying the probability of occurrence of a predetermined hemodynamic event, and applying a selected one of the plurality of available therapies for treatment of the predetermined hemodynamic event when the cumulative scoring of the processed subparameters reaches a preestablished level of probability that a hemodynamic event is occurring which requires the selected therapy. In the preferred method the other physiologic parameter being detected represents physical activity of the patient, and the subparameters obtained from the processing step for that parameter may include patient rest, patient exercise, patient position, and/or change of patient position.

Thus, the method of controlling the therapeutic function of the implantable antitachycardia device may include detecting the posture, position or physical activity of the patient by use of one or more accelerometers carried by the patient, "carried" meaning that the accelerometer(s) may be implanted or, alternatively may simply be worn externally by the patient. The posture, position or physical activity of the patient detected by the accelerometer(s) may be used for comparison against the ECG of the patient to determine whether the patient is experiencing a physiologic tachycardia or a pathologic tachycardia, and, in the latter event, an appropriate antitachycardia therapy is applied from the device.

The method of the invention also includes monitoring the cardiac activity and current status of physical activity or inactivity of the patient following the delivery of an antitachycardia therapy to determine whether that delivered therapy protocol succeeded in terminating the pathologic tachycardia, and delivering another antitachycardia protocol different from the last delivered therapy protocol when the monitoring indicates that the last delivered protocol did not terminate the pathologic tachycardia. The selection of the next antitachycardia therapy protocol following the determination that the last protocol did not succeed, may be made from a group of known cardiac pulse and shock therapies or protocols for breaking VT and VF, programmed into the interventional device, such as one or more bursts of stimulating pulses, a train of rapid stimulation pulses, one or more low energy shocks, and a relatively higher energy defibrillating shock. If the VT progresses, the next therapy or protocol selected would typically be more drastic than the last, ranging ultimately up to an appropriately phased high energy defibrillating shock.

BRIEF DESCRIPTION OF THE DRAWINGS

The above and other objects, aspects, features and attendant advantages of the present invention will become apparent from a consideration of the following detailed description of a presently preferred embodiment and method, taken in conjunction with the accompanying drawings, in which:

FIG. 1 is a graph or chart illustrating readouts measured in g versus time from an activity status sensor implanted in a patient;

FIG. 2 is a graph of the change in g relative to time for an event constituting a sudden vigorous movement by the patient;

FIGS. 3A and 3B are perspective representations of a pair of mercury ball sensors in fixed orthogonal orientation as implanted in a patient, and an accelerometer fabricated in an integrated or hybrid electronic circuit, respectively;

FIG. 4 is a graph contrasting the output of a mercury ball sensor in number of contact changes per unit of time, for a patient during walking and during a syncope;

FIG. 5 is simplified depiction of an implantable medical interventional device with activity status sensor(s) located within the device housing;

FIG. 6 is a graph or chart of sensor contact changes with time relative to numbered contacts for walking and a syncope, as detected by an activity status sensor of the mercury ball type;

FIG. 7 is a plot of the quotient of the standard deviation relative to the mean of the output signal of the activity status sensor, for walking and syncope;

DESCRIPTION OF THE PREFERRED EMBODIMENT AND METHOD

Figure 8:
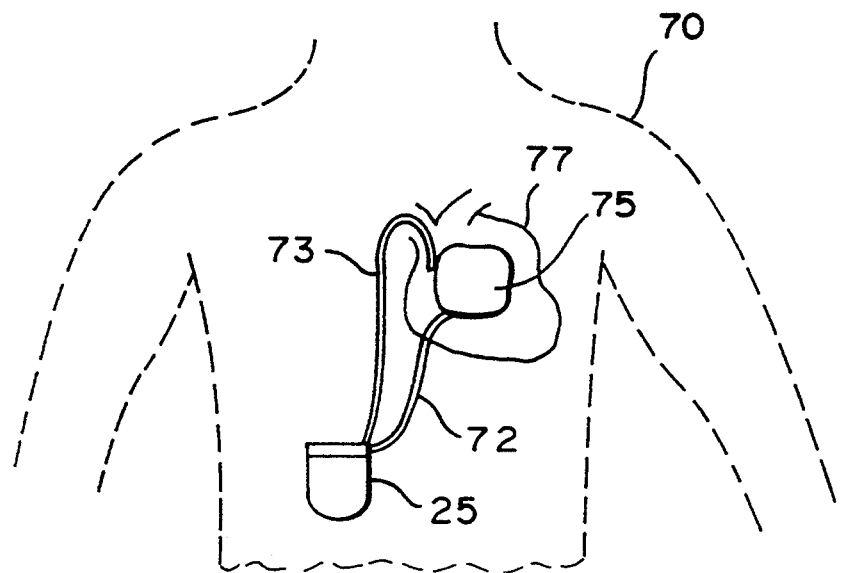
FIG. 8 is a phantom view of a patient with an implanted interventional device according to the invention.

In the preferred embodiment and method of the invention, the implantable interventional device utilizes not only a direct sensor of cardiac activity such as an ECG sensor, but also an activity status sensor adapted to detect the position and movements of the patient, preferably an accelerometer or other electromechanical converter, which may be calibrated for both static and dynamic outputs. The static output will depend upon the physical position or posture of the implant patient when inactive (e.g., at rest, or in a state of collapse). Assume that the activity status sensor is oriented vertically when implanted, and in that position produces a zero g (i.e., unit of gravity) output. The sensor produces a +1 g output in one aspect of its horizontal orientation, (i.e., one major side down), and produces a −1 g output in the opposite aspect of horizontal orientation (the other major side down).

In this example, illustrated by the chart of FIG. 1, the activity status sensor provides a zero reading when the patient is standing during a first time interval, a +1 when the patient is supine during a second time interval, and a −1 when the patient is prone during a third interval. This chart is not intended to show the response of the activity status sensor to changes in position, such as in the period between the first and second intervals, but only that different readouts or signals are produced by the sensor upon detection of different static positions of the patient.

The particular outputs may be modified by calibrating the sensor for slight deviations of orientation relative to these three positions. If the patient were lying on her side, the sensor reading would not be +1 or −1, but a non-zero value. By calibrating the electrical output of the sensor circuit after implantation, the orientation of the sensor in any position of the patient will be known from the readout. By employing a second such activity status sensor with a 90° orientation relative to the first sensor, each sensor recognizes two of the three mutually orthogonal axes (X-Y-Z) in three dimensional space, and both together detect a full three axis orientation, to provide a combined reading uniquely identifying the patient's position. Thus, the sensor may be used to detect static or stable (i.e., non-moving) position of the patient, and also to detect patient activity constituting dynamic movements of the patient, such as a momentary change of position or continuing movements such as walking, dancing, bicycling, and so forth.

If the patient's position were to change suddenly from standing up to lying down, the activity status sensor output would undergo change from a reading of 0 to +1, which could indicate a syncope. There are other possibilities, of course, such as tripping and falling, or merely consciously dropping quickly on a bed. As will be discussed in greater detail presently, the fact that other possibilities exist, even in a situation where one sensor, such as the activity status sensor, is used for confirmation or reinforcement of another sensor—e.g., an ECG sensor—leads to the use, according to another aspect of the invention, of a scoring system or other evaluation system by which to assess the probability that the patient is experiencing a VT, a fast VT, or fibrillation, by evaluating the signals of both sensors not only instantaneously but over time.

By analyzing the activity status signal(s), the particular position, ongoing state of activity, or mere sudden change in position of the patient can be detected with considerable precision. For example, if the patient is standing and at rest, the sensor output is 0; but if he suddenly collapses, the sensor responds with a relatively large spike output. If the actual value of the change, delta g over time ( g/t), is calculated, or the quotient of the standard deviation and the mean of the continuously monitored activity status signal is computed for that period, it becomes quite apparent that a dramatic event has occurred, as shown in FIG. 2.

Concurrent detection of the patient's cardiac activity exhibiting a rapid heart rate along with such an assessment of the activity status signal would indicate a pathological tachycardia—either a very rapid VT or even VF, with apparent loss of consciousness by the patient. The implanted interventional device would be programmed to respond automatically in these circumstances by immediately delivering an appropriate treatment. For example, the device would commence charging its output capacitors to an appropriate level and, upon reaching that level, deliver the predetermined (programmed) electrical waveform therapy, constituting a single or multiple phase shock of appropriate energy content, to the patient's heart. The distinct advantage achieved in this situation is that precious seconds are saved, the loss of which might otherwise have caused a fatality.

It will also be seen that these detection techniques provide improved discrimination between physiologic tachycardia and pathologic tachycardia, which can overlap at heart rates ranging from about 130 to about 180 bpm, than has heretofore been achieved. Indeed, a serious problem that occurs with ECG detection alone is such overlap between the rates for a fast physiologic tachycardia and a relatively slow pathologic VT. Some patients experience slow VT while under medication, and are at risk that, although of relatively slow rate at the moment, this dangerous tachycardia may develop (accelerate) into fibrillation. Normally, VF occurs only after VT; it is rare that the person will experience VF which is not precipitated by a pathologic tachycardia. The implantable interventional device may be programmed to respond to a sensed ECG signal indicative of possible slow VT, coupled with confirmation by the activity status signal indicative of either collapse or physical inactivity of the patient, by stimulating the heart with low energy shocks to break the VT and prevent VF from developing. Alternatively, the programming philosophy may represent a less conservative approach in which the slow tachycardia and lack of physical activity of the patient merely define an alert condition of the device in which the capacitors are charged to the proper energy level, in anticipation of the possibility that a more dramatic situation may develop. If it then happens that the delivery of an antitachycardia or defibrillating shock is warranted, precious time will not have been lost waiting for the output storage capacitors of the device to be charged.

Advantageously, the use of two complementary sensors in this manner serves not only to control charging and firing of the implantable interventional device for treatment of tachycardias and fibrillation, but also to better evaluate the probability of success of interventional measures. Since VT normally can be broken by lower energy doses (pulses) discharged from a device to the heart than the magnitude of energy needed to terminate VF, a considerable energy saving is achieved which helps to reduce the size of the battery and, thus, of the implanted device, or to increase its lifetime with the same battery capacity. These are important goals in the development of any battery-powered implanted medical device.

It should be emphasized, of course, that numerous conventional electrical waveform therapies or therapy protocols may be programmed into the interventional device for selective application to the heart upon detection of an applicable cardiac event from the complementary sensors. For example, these may include single stimulating pulses, stimulating pulse sequences, stimulating pulse trains of variable repetition frequency, one or more bursts of stimulating pulses, and single phase or multiple phase shocks of variable energy content generally greater than the energy content of the pulses in the other protocols which are utilized for treatment. In general, the therapy is applied in successively more stringent protocols until it is successful to break the VT or VF.

Both the degree of difficulty and the likelihood of failure in achieving defibrillation increase with the length of time that the patient is in fibrillation. It is crucial to reduce to the maximum practicable extent the time interval from onset of fibrillation to delivery of the initial shock, from the standpoints of both the energy required to defibrillate the heart and the opportunity to successfully defibrillate and resuscitate the patient. It is considerably easier to interrupt a VT, which may require delivery of only one joule of electrical energy, than to terminate VF with the potential requirement of 15 joules or more in each shock. Correspondingly, resuscitation is much more achievable with a patient who has been in fibrillation for only a few seconds than with one whose attack has continued for several minutes. Prompt application of treatment is also important with a patient who is experiencing either VT or VF and is fighting against loss of consciousness. If the interval from onset to delivery of therapy is excessive, e.g., ten to thirty seconds, the patient may begin to faint, whereas if intervention had taken place earlier the circulatory system would have been better able to compensate for the fast heart rate without the patient losing consciousness.

The type of dual sensing used according to the present invention aids the implanted programmable microprocessor-based interventional device to better interpret the ECG criteria normally applied to detect pathologic tachycardias (e.g., heart rate, morphology of the ECG, sudden onset, rate stability, etc.), because the activity status sensor is complementary, providing additional information concerning the cardiac event under scrutiny, rather than merely part of the ECG criteria. The speed with which a better understanding and interpretation of the ECG is obtained, through the use of this complementary sensor, vastly improves the patient's chances of survival by virtue of the lower energy requirement and higher probability of resuscitation. The activity status sensor not only increases the probability of detection compared to the use of an ECG sensor alone, with resulting faster response, but also improves discrimination between physiologic and pathologic tachycardias especially in the borderline region from 130 bpm to 180 bpm, thereby better avoiding needless, painful and debilitating shocking of the heart.

Preferably, the activity status sensor is of the mercury ball type described in U.S. Pat. No. 4,846,195. Although a single sensor may be used, it would constitute only an X-Y axes (two dimensional) detector incapable of uniquely identifying position. For reasons mentioned earlier herein, it is preferred that two such sensors with fixed orthogonal orientation for combined detection of all three axes (X-Y-Z) of potential direction of movement or position of the patient be used. Referring to FIG. 3A, sensor 10 includes a pair of mercury ball sensors 12 and 13 coupled together at an angle of 90 degrees. This fixed orientation of the two assures that their combined output signal will properly identify different specific physical positions of the patient even if the overall sensor were to undergo a shift in its orientation after implantation in the patient's body.

It is desirable, however, that the orientation of the sensors after implantation be such that one of them (sensor 13, in this example) is approximately horizontal and the other (here sensor 12) approximately vertical when the patient is standing upright. In the exemplary configuration represented in FIG. 3A, sensor 12 is somewhat smaller than and assembled within sensor 13 in the fixed relationship. In practice, the two position sensors may be separated, but nevertheless fixed in their orthogonal orientation. Under static (motionless) conditions of either sensor of the pair, the mercury ball (not shown) is at rest and contacts specific ones among the set of electrodes (electrical contacts) 14 disposed about the side or floor of the sensor chamber. The electrodes are connected by respective electrical conductors to the output circuit of the sensor, each set of electrode locations in conductive contact identifying a particular position of the patient. As the patient changes position or engages in ongoing physical activity, one or both mercury balls will roll about within their respective chambers and make and break contact with the electrodes. The combined static locations of the mercury balls within the sensor pair, or their dynamic locations as they make and break connections between adjacent electrodes (closures and openings with time) is detected to provide information regarding the physical position, change in position, and ongoing movements of the patient.

Alternatively, the activity status sensor may be an accelerometer which is fabricated in silicon or other semiconductor material within an integrated electronic or hybrid circuit, such as that described in U.S. Pat. No. 5,031,615. A hybrid semiconductor integrated circuit incorporates the accelerometer as a microminiature mechanoelectrical converter or transducer of high efficiency and low power consumption. This type of accelerometer 15, shown in FIG. 3B, has a silicon monocrystalline substrate 15-1, an epitaxial doped layer 15-2 overlying the surface of substrate 15-1, and a polycrystalline silicon layer 15-3 sandwiched between passivating layers 15-4, 15-5 of silicon dioxide. A cavity 15-6 is formed in the substrate by etching, and portions of the silicon and passivating layers are removed, forming a rectangular plate 15-7 connected by four arms to the corners of the cavity. The plate and its arms constitute the acceleration responsive element. An additional layer may be provided on the structure with an opening contiguous with the cavity to allow axial movement of plate 15-7 on its arms, and a protective layer of glass disposed over the structure. An integrated circuit suitable for processing the movements of the plate in response to acceleration to provide the activity status signal may be fabricated in the silicon substrate, within the region generally below that designated by 15-8, by conventional semiconductor processing techniques.

In FIG. 4, curve 17 represents the number of contact changes per second (along the ordinate) in the horizontal mercury ball sensor 13 of FIG. 3A relative to elapsed time in seconds (along the abscissa) for a subject wearing the sensor and walking at a rate of 3.2 kilometers per hour (kin/h) on a 0% grade. Although only one sensor output is indicated, similar results are obtained for the vertical sensor, albeit they may be larger or smaller signals depending on extent of movement for its orientation. The activity status signals from the sensors are processed with identification of each contact of each sensor, the number of contact closures and openings for each contact, and the instant of time at which each closure or opening took place within a specified time interval. It will be observed that when the patient is walking, the output of the mercury ball sensor (each sensor) is relatively smooth. In contrast, curve 20 illustrates the output signal produced by the sensor with the subject feigning collapse (corresponding to a patient experiencing a syncope). This large spike considerably exceeds the number of contact changes with time that occurred during a corresponding interval for walking.

Figure 10:
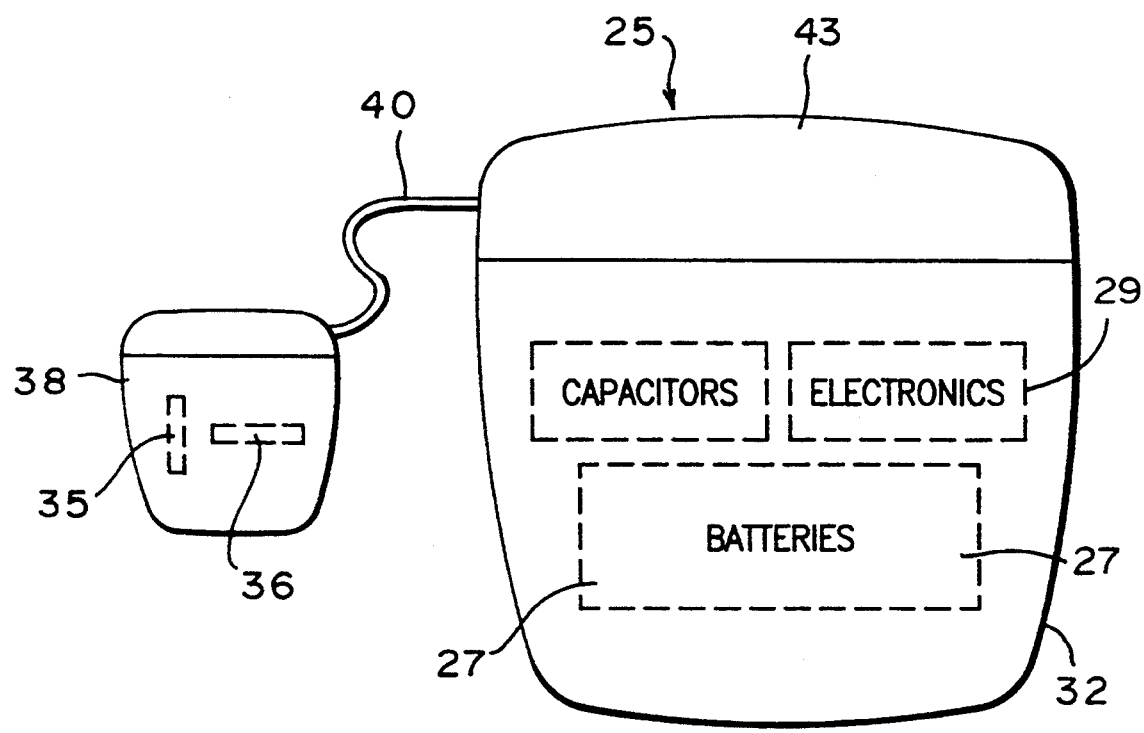
FIG. 10 is similar to FIG. 5, except for the inclusion of an alternative arrangement in which the sensor is housed in its own separate case and connected by an electrical lead to a connector on the device housing.

FIG. 5 is a simplified diagram of an implantable interventional device such as defibrillator 25 which is of conventional construction, except as will be noted presently, to provide both antitachycardia and defibrillation therapies. The defibrillator components including batteries 27, electronics 29 (e.g., including a microprocessor, memories, etc.) and output capacitors 30 for storing electrical charge in variable quantities according to the amount of electrical energy to be delivered for shocking the heart to provide the desired therapy. According to the invention, an activity status sensor is incorporated within the defibrillator in the form, for example, of orthogonally oriented mercury ball sensors 35, 36 substantially as described in FIG. 3A except that the two may be separately affixed to maintain that orientation. The two are housed within but mechanically isolated from the case 32 which houses all of the other components of the defibrillator, to avoid sensitivity merely to pressure on the case. Alternatively, the sensor pair may be housed in its own biocompatible hermetically sealed case 38 for implantation in the patient in a location separate from the defibrillator case, as shown in FIG. 10, in which like components are designated by like reference numbers.

The lead 40 for connecting the separately housed sensor implant 38 to the electronic control circuitry of the implanted defibrillator 25 may be a multiple contact type such as that disclosed in U.S. Pat. No. 4,971,057, to facilitate the signal processing. The defibrillator case 32 includes a header 43 with electrical connectors for the lead associated with the activity status sensor implant (if in a separate implantable case) and for the lead(s) connected to the defibrillating and other electrodes for delivering therapy and sensing cardiac activity. An ECG sense amplifier and related processing circuitry included within electronics 29 of the defibrillator provide an ECG signal for detecting rapid heart rates and other cardiac activity.

In operation, the implantable medical interventional device (defibrillator 25, in this example) is adapted to intervene upon detection of cardiac activity of the implant patient indicative of VT or VF by successively applying to the heart selected ones of several different preprogrammed electrical waveforms conventionally utilized as protocols for treatment to break VT or VF, respectively, until the monitored cardiac activity indicates that the treatment has been successful. The activity status sensor detects physical activity and inactivity of the patient to complement detection of the patient's cardiac activity for confirming that a detected VT is a pathologic tachycardia rather than a physiologic tachycardia. The microprocessor in the device responds to such confirmation to select an appropriate one of the preprogrammed protocols stored in memory for treatment, with application of the selected electrical waveform to the heart via the output circuit of the device and the leads. In the example of the defibrillator, the shocks intended to defibrillate the heart are produced by charging the output capacitors of the device to the predetermined energy level, and then discharging them through the heart in the desired phased waveform, in a conventional manner. Certain other aspects of the device operation will be addressed in the description of FIG. 8 below.

FIG. 6 is a chart of the number of contact changes with time (ten second intervals) plotted on the ordinate against the designated numbered contacts of each sensor on the abscissa for walking (curve 52), slight position changes (curve 50) and feigned syncope (curve 54) of a healthy volunteer subject carrying a horizontally-disposed mercury ball sensor. Despite the relatively small number of contact changes with time for the syncope compared to an activity such as walking, when plotted against time, as in FIG. 4, the maximum value of the syncope significantly exceeds that of the walking activity.

FIG. 7 is a bar chart or plot of the quotient of the standard deviation divided by the mean of the signal produced by the horizontal mercury ball sensor for walking and collapse, and illustrates the clear distinction of a syncope from other types of physical activity by this technique. For the walking activity (bars 60) the discrete calculations produce consistently low values. In contrast, the syncope (bars 62) has considerably larger discrete values and average value.

By calculating the quotient of the standard deviation (the variance) and the mean of the changes of contact "makes" and "breaks" by the moving mercury ball of the sensor, continuing activity can be discriminated from sudden changes of position, regardless of the extent of the changes over time. The standard deviation relative to the mean is a low value for ongoing activity, and a high value for brief random movements or noise. Hence, this calculation can be used to clearly differentiate between signals which are relatively continuous and signals which are attributable to sudden brief vigorous movement, for example a collapse with loss of consciousness. All calculations are readily performed by the microprocessor of the device.

Heretofore, the inability to fully assess the hemodynamic consequences of a tachycardia in different patients has made it difficult to provide a device universally adaptable to determine whether and when a particular antitachycardia therapy should be delivered. One patient may be able to tolerate an elevated heart rate of 180 bpm with a rapid decline of systolic blood pressure to 65, for example, whereas another patient, because of stenosis and weak cerebral profusion, may suffer loss of consciousness and respiratory functions with a tachycardia rate of 160 bpm and systolic blood pressure of 70. Measurements of heart rate, stroke volume, cardiac output, and even blood pressure do not fully delineate cerebral status for each individual patient. Hemodynamic parameters may appear to be within a normal range or not life-threatening, but they do not provide a true indication of the cerebral function of the patient.

With the present invention, by comparing the ECG signal with the activity status signal, however, the occurrence of a slow pathologic tachycardia is recognized by the fact that the elevated heart rate is present with little or no physical activity by the patient, as distinguished from a physiologic tachycardia where coincidence of rapid heart rate and pronounced physical activity is evident from the outputs of the two types of sensors. Also, loss of consciousness by the patient is readily detected from the above-described calculation performed by the microprocessor, of variances relative to mean of the activity status signal to indicate the need for a more drastic therapy in response to a dramatic cardiac event (e.g., syncope). Thus, in the system of the present invention, in addition to the improved discrimination of pathologic versus physiologic tachycardias, the detection system provides an indication of hemodynamic consequences which warrant application of a specific antitachycardia therapy.

FIG. 8 illustrates the defibrillator 25 implanted in a patient 70, with lead/electrode assemblies 72, 73 for an epicardial patch electrode 75 and an endocardial counter-electrode (not shown). The patch electrode overlies an appropriate region of the epicardium and the counter-electrode in positioned in the right ventricle, for efficient delivery of the high voltage, high energy shock waveform to the heart 77. Implantable defibrillation apparatus of various types is known in the art, and the specific type is not critical to the implementation of the present invention except as otherwise expressly stated herein.

The control means of the conventional microprocessor of the device includes computing means responsive to detected physical activity of the patient by the activity status sensor for recognizing from the detected activity the occurrence of a sudden vigorous movement associated with a syncope by calculating the variances relative to the mean of the detected physical activity. The microprocessor control means further includes activation means which responds to such recognition for selecting a defibrillating electrical waveform therapy or protocol for immediate application to the patient's heart.

The system and method of the invention further provide a tallying technique by which subparameters of the detected cardiac activity and the detected physical activity or inactivity (or other sensed physiologic parameters, as stated earlier herein) are weighted according to their respective significance in identifying the cardiac events of interest, to determine from the total weighting in a given interval of time (including, in the lower limit, an interval which is substantially instantaneous) the likelihood that physiologic tachycardia, pathologic tachycardia, or fibrillation is being detected in that interval.

Figure 9:
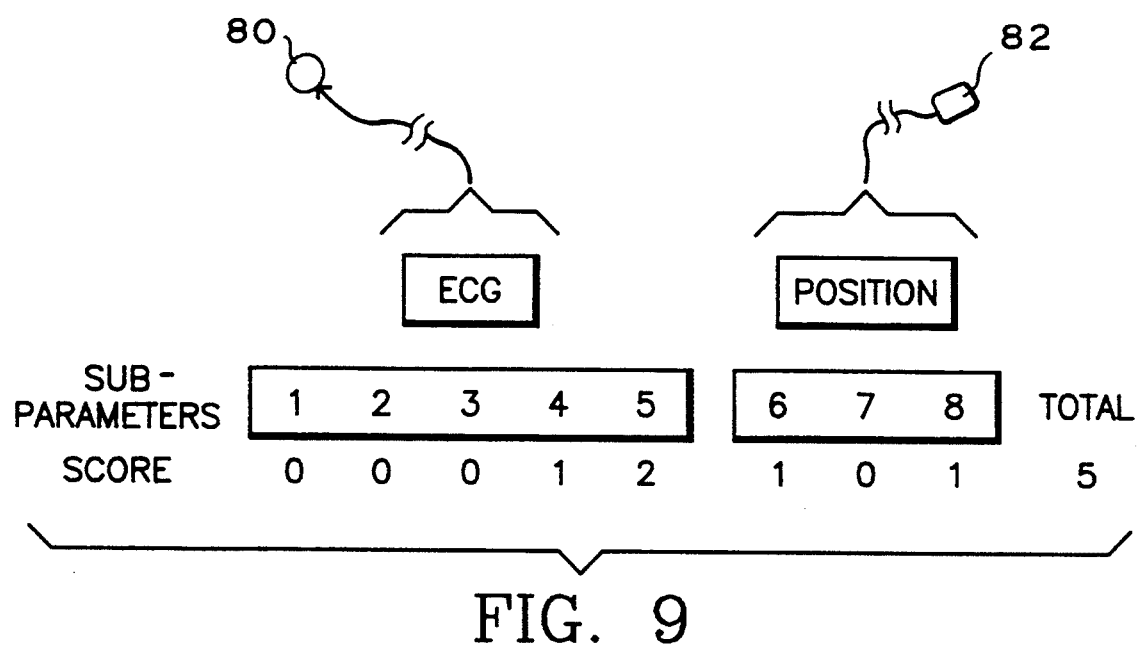
FIG. 9 illustrates an exemplary scoring technique to aid in determining the specific nature of the cardiac event being detected and, accordingly, the type of therapy or treatment to be delivered where the event is VT or VF.

FIG. 9 is a simplified diagram illustrating such a scoring system for enhancing the probability of detecting a cardiac event requiring antitachycardia therapy, including, among other protocols, defibrillating shocks. A number of subparameters of the sensed cardiac activity and physical activity or inactivity (from sensors 80 and 82) may be designated for use in this system. For example, subparameters 1 through 5 may be (1) absolute heart rate or absence of QRS complexes, (2) relative heart rate change in absolute numbers (bpm), (3) relative heart rate change over time (bpm/time), (4) rate stability, and (5) ECG morphology criteria. These subparameters may be assigned possible scores ranging from one to ten each, depending on their relative importance, sensitivity and specificity, and the extent to which they correspond to criteria indicative of a cardiac event requiring an available therapy. Other subparameters 6, 7 and 8 may be scored, for example, based on (6) patient rest or activity (exercise), (7) patient position, and (8) change of position.

The individual subparameter scores are tallied and, for example, a total score of up to 20 is programmed to indicate a high probability of a slow VT, a total score of 20 to 30 to indicate a fast VT, and a total score exceeding 30 to indicate VF. The programming of the implanted device may now be set up to respond to scores within the established ranges by delivering the appropriate therapy including operation selecting whether the device charges its output capacitors to deliver a pulse or pulses having up to the maximum energy level or some predetermined lower level. In the specific example of FIG. 9, subparameters 1-5 which are allocated to the ECG signal have respective scores of 0, 0, 0, 1, 2, and subparameters 6-8 which are allocated to the activity status signal have respective scores of 1, 0, 1. Here, the total score is 5, which indicates a sufficiently slow heart rate as to not require the delivery of antitachycardia therapy by the device at this time. Continued monitoring by the complementary sensors may lead to scoring changes that will determine whether therapy should be applied.

Although certain preferred embodiments and methods have been disclosed herein, it will be apparent to those skilled in the art from a consideration of the foregoing description that variations and modifications of the described embodiments and methods may be made without departing from the true spirit and scope of the invention. Accordingly, it is intended that the invention shall be limited only to the extent required by the appended claims and the rules and principles of applicable law.

We claim:

1. An implantable medical interventional device for treatment of pathologic tachycardias, comprising:
    first sensor means adapted to detect cardiac activity of the patient in which the interventional device is implanted for producing a first electrical signal representative of such cardiac activity including heart rate of the patient,
    second sensor means adapted to detect movement and lack of movement indicative of physical activity and inactivity of the patient for producing a second electrical signal representative of the patient's activity status,
    generator means for selectively generating electrical waveforms to be applied to the patient's heart to break a pathologic tachycardia, and
    control means setting a predetermined heart rate and responsive to said first and second electrical signals as complementary criteria for distinguishing a heart rate of the patient exceeding the predetermined rate during a period of physical activity by the patient indicative of a pathologic tachycardia requiring treatment from a physiologic tachycardia attributable to patient activity, and including activation means responsive to a decision by said control means that the patient is experiencing a pathologic tachycardia for triggering said generator means to generate an electrical waveform having characteristics selected to break the tachycardia.

2. The implantable medical interventional device of claim 1, wherein:
    said first sensor means comprises a sensor for detecting and generating a signal representative of the patient's ECG.

3. The implantable medical interventional device of claim 1, wherein:
    said second sensor means comprises an accelerometer.

4. The implantable medical interventional device of claim 3, wherein:
    the accelerometer comprises means to detect orientation and movement of the patient in three dimensions.

5. The implantable medical interventional device of claim 4, wherein said means to detect orientation and movement of the patient in three dimensions comprises:
    first and second mercury ball sensors, each including a mercury ball and a multiplicity of spaced-apart electrodes in a plane over which the respective mercury ball may roll in response to movement of the patient for intermittently establishing electrical connections with various ones of the electrodes, and said electrode planes of said first and second mercury ball sensors being orthogonally oriented relative to one another to enable detection of movement and orientation of the accelerometer along three different orthogonal axes.

6. The implantable medical interventional device of claim 5, wherein said control means further includes:

detection means responsive to electrical closures and openings of the spaced-apart electrodes in each of said first and second mercury ball sensors as the respective mercury ball makes and breaks electrical connections with various ones of said spaced-apart electrodes during rolling of the ball, and distinction means for calculating the quotient of the standard deviation divided by the mean of the closures and openings over a predetermined interval of time to detect sudden brief movement by the patient consistent with a syncope for enhancing the decision by said control means that the patient is experiencing a pathologic tachycardia.

7. The implantable medical interventional device of claim 3, further including:

a case housing said device, and means mechanically isolating said accelerometer from the case to render the accelerometer substantially unresponsive to pressure on the case.

8. The implantable medical interventional device of claim 1, wherein:

said second sensor means comprises integrated electronic circuit means responsive to orientation and movement thereof for producing said second electrical signal.

9. The implantable medical interventional device of claim 8, wherein:

said integrated electronic circuit means is a silicon based mechanoelectrical converter.

10. The implantable medical interventional device of claim 9, wherein:

said mechanoelectrical converter is selected from the group consisting of piezoresistive, piezoelectric and piezocapacitive converters.

11. The implantable medical interventional device of claim 1, wherein:

said control means is further responsive to said complementary criteria for deciding whether the patient is experiencing ventricular fibrillation, said generator means includes storage capacitor means for storing a level of electrical charge suitable for defibrillation of the patient's heart, and said activation means is responsive to a decision by said control means that the patient is experiencing ventricular fibrillation for causing said storage capacitor means to be charged to said level for delivery within said electrical waveform when the generator means is triggered by the activation means.

12. The implantable medical interventional device of claim 1, wherein said control means further includes:

calculating means responsive to said second electrical signal representative of the patient's activity status for calculating the standard deviation relative to the mean of said second electrical signal over a predetermined time interval for enhancing discrimination of pathologic tachycardia from physiologic tachycardia by said control means.

13. In combination with an implantable defibrillator adapted to selectively deliver electrical waveform therapies to a patient's heart in response to detection of cardiac activity indicative of ventricular tachycardia or fibrillation, the improvement comprising:

control means for discriminating between pathologic tachycardia and physiologic tachycardia during the patient's engagement in physical activity, said control means including implantable complementary sensor means for detecting movement indicative of physical activity of the patient, computing means responsive to detected physical activity and confirming detected cardiac activity of the patient indicative of pathologic tachycardia for recognizing a sudden brief movement by the patient as syncope, and generator means responsive to recognition of syncope by said computing means for generating a predetermined antitachycardia electrical waveform therapy to be delivered to the patient's heart to revive the patient.

14. The improvement of claim 13, wherein:

said complementary sensor means includes means for producing an electrical signal in response to detecting movement indicative of physical activity of the patient, and said computing means includes means for calculating the quotient of the standard deviation divided by the mean of variations of said electrical signal with the detected movement over time.

15. The improvement of claim 13, wherein:

said complementary sensor means comprises accelerometer means for sensing movement of the patient along three mutually orthogonal axes.

16. The improvement of claim 15, wherein the accelerometer means comprises:

a pair of orthogonally oriented mercury ball sensors each including spaced-apart planar electrodes and a mercury ball for contacting various ones of said spaced-apart electrodes to intermittently establish and disrupt electrical connections therewith over time and to establish particular electrical connections therewith at any given time upon positioning of the respective mercury ball in response to movements and static position of the patient.

17. A method of timing the delivery of antitachycardia and defibrillating electrical therapies to a patient's heart from an automatic implanted defibrillator device, comprising the device-implemented steps of:

detecting the current status of the patient's physical activity while simultaneously detecting the patient's cardiac activity to recognize a ventricular tachycardia while the patient is engaged in physical activity, determining the degree of probability that the recognized ventricular tachycardia is a pathologic tachycardia rather than a physiologic tachycardia by weighting the detected cardiac activity and the detected status of physical activity of the patient as separate indicia of the degree of probability that a pathologic tachycardia is occurring, and delivering an antitachycardia electrical therapy to the patient's heart when the weighting indicates a predetermined degree of probability that a pathologic tachycardia is occurring.

18. The method of claim 17, further including the device-implemented steps of:

detecting whether the antitachycardia electrical therapy delivered to the patient's heart was effective to terminate the tachycardia, and, if not, whether the tachycardia is accelerating into ventricular fibrillation, and delivering defibrillating electrical therapy to the patient's heart if the previously delivered antitachycardia electrical therapy was ineffective to terminate the tachycardia coupled with detection of acceleration into ventricular fibrillation.

19. The method of claim 17, further including the device-implemented steps of:

monitoring the cardiac activity and the current status of physical activity or inactivity of the patient following the delivery of an antitachycardia electrical therapy to determine whether that delivered therapy succeeded in terminating the pathologic tachycardia, and delivering another antitachycardia electrical therapy different from the last delivered therapy when the monitoring indicates that the last delivered therapy did not terminate the pathologic tachycardia.

20. The method of claim 19, wherein the step of delivering another antitachycardia electrical therapy includes:

selecting said another antitachycardia electrical therapy to be delivered from the group consisting of a single burst of stimulating pulses, plural bursts of stimulating pulses, a train of rapid stimulation pulses, a single low energy shock, plural low energy shocks, and a relatively higher energy shock, and generating the selected another antitachycardia electrical therapy for delivery to the patient's heart.

21. An implantable medical device for intervention in response to the implant patient experiencing a syncope, comprising:

first sensor means for detecting electrical cardiac activity of the patient and for producing a first electrical signal representative thereof, second sensor means for detecting posture, position and physical activity of the patient and for producing a second electrical signal representative thereof, discrimination means responsive to said first and second electrical signals for discriminating between a physiologic tachycardia and a pathologic tachycardia of the patient's heart, control means responsive to discrimination of a tachycardia by said discrimination means as a pathologic tachycardia for prescribing one among a plurality of different electrical therapy waveforms for treatment of the pathologic tachycardia, and generator means responsive to the prescribing of one of said electrical therapy waveforms by said control means for generating the prescribed waveform for application to the patient's heart, said discrimination means including computing means responsive to said second electrical signal representative of detected physical activity of the patient by said second sensor means for recognizing therefrom the occurrence of a collapse of the patient associated with a syncope, said control means including means responsive to said recognizing by said computing means for prescribing defibrillating waveform from among said plurality of electrical therapy waveforms for treatment of the syncope.

22. The implantable medical device of claim 21, wherein:

said computing means includes means responsive to said second electrical signal representative of detected physical activity of the patient by the second sensor means, and representative of detected changes of position of the patient having a mean value over a time interval and undergoing variances from the mean value, for calculating from said second electrical signal the variances relative to the mean value thereof to enhance recognition of a syncope event.

23. The implantable medical device of claim 22, wherein:

said second sensor means comprises accelerometer means for sensing movement of the patient along three mutually orthogonal axes.

24. The implantable medical device of claim 21, wherein:

said first electrical signal has a plurality of parameters associated with at least the patient's heart rate and ECG, said second electrical signal has a plurality of parameters associated with at least the patient's posture, position and change thereof, and activity, and said computing means includes tallying means responsive to said parameters of said first and second electrical signals for assigning predetermined weighted Values to said parameters according to the relative importance of each Of said parameters in assessing probability that a cardiac event including at least one of pathologic tachycardia and syncope is occurring based on detection by the respective sensor means, and for adding the weighted values of the parameters for determining from the total of said weighted values over a predetermined interval of time the likelihood that a syncope is occurring in that interval of time.

25. A method of determining when to apply any of a plurality of available antitachycardia therapies, including possible defibrillation therapy, to a patient's heart from an implantable antitachycardia device, comprising the steps of:

providing said plurality of antitachycardia therapies, detecting at least two different physiologic parameters of the patient from which hemodynamic events for treatment with said therapies are discernible, one of said parameters representing electrical cardiac activity of the patient, processing the detected different physiologic parameters to obtain a variety of subparameters identifying characteristics of the respective detected different physiologic parameters from which said subparameters were obtained, scoring each of the processed subparameters by assigning to it a relative value according to its importance in signifying the probability of occurrence of a predetermined hemodynamic event, and adding the relative values of the processed subparameters to obtain a cumulative score, and selecting one of the provided plurality of anti-tachycardia therapies prescribed as best suited for treatment of the predetermined hemodynamic event when the cumulative score of the processed subparameters reaches a preestablished level of probability that said predetermined hemodynamic event is occurring.

26. The method of claim 25, including:

designating movement indicative of physical activity of the patient as another of the at least two different physiologic parameters to be detected.

27. The method of claim 26, wherein:

the step of processing the detected different physiologic parameters to obtain a variety of subparameters is performed to obtain subparameters including at least one of patient rest, patient exercise, patient position, and change of patient position for the parameter indicative of patient movement, and to obtain subparameters including at least one of absolute heart rate, absence of QRS complexes, relative heart rate change, heart rate stability, and ECG morphology for the parameter representative of cardiac activity.

28. A method of controlling the delivery of an appropriate therapy of an antitachycardia device configured and adapted to be implanted in a patient, which includes:

monitoring the posture, position and physical activity of the patient by use of at least two two-dimensional accelerometers carried by the patient to detect movement of the patient along three mutually orthogonal axes, detecting the patient's ECG, processing the detected movement of the patient to obtain information on posture, position and physical activity of the patient, and processing the detected ECG of the patient to obtain information thereon, using the information obtained from both detected movement and detected ECG and a comparison thereof to distinguish a physiologic tachycardia from a pathologic tachycardia of the patient's heart, and, if a pathologic tachycardia is found, triggering the antitachycardia device to deliver a predetermined therapy therefrom predetermined as most appropriate to terminate the pathologic tachycardia.

29. A control device for controlling the therapeutic function of an antitachycardia device configured and adapted to be implanted in a patient, said control device including:

accelerometer means for detecting state of physical activity of the patient and at least one of posture and position of the patient, and ECG means for detecting the ECG of the patient, verification means for comparing the detected state of physical activity of the patient and said at least one of posture and position of the patient against the detected ECG of the patient to distinguish a physiologic tachycardia from a pathologic tachycardia of the patient's heart, and trigger means for actuating said antitachycardia device to apply a preselected antitachycardia therapy to the patient upon determination that the patient is experiencing a pathologic tachycardia.

* * * * *